US009613786B2

(12) United States Patent
Yao (10) Patent No.: US 9,613,786 B2
(45) Date of Patent: Apr. 4, 2017

(54) PEAK DETECTION METHOD FOR MASS SPECTROMETRY AND SYSTEM THEREFOR (71) Applicant: SHIMADZU CORPORATION, Kyoto-shi, Kyoto (JP)

(72) Inventor: Jingwen Yao, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 784 days.

(21) Appl. No.: 13/872,466

(22) Filed: Apr. 29, 2013

(65) Prior Publication Data
US 2013/0311109 A1 Nov. 21, 2013

Related U.S. Application Data
(60) Provisional application No. 61/639,748, filed on Apr. 27, 2012.

(30) Foreign Application Priority Data
Nov. 2, 2012 (JP) ................. 2012-243103

(51) Int. Cl.
G01N 31/00 (2006.01)
H01J 49/00 (2006.01)
G06F 19/00 (2011.01)

(52) U.S. Cl.
CPC ........ H01J 49/0036 (2013.01); G06F 19/703 (2013.01); G06F 19/707 (2013.01)

(58) Field of Classification Search
CPC .... G06K 9/0053; G06F 19/703; G06F 19/707
See application file for complete search history.

(56) References Cited

U.S. PATENT DOCUMENTS 7,884,318 B2 * 2/2011 Milgram ............ G01N 30/8651
250/281
8,658,971 B2 * 2/2014 Green .................. G06K 9/0053
250/281

FOREIGN PATENT DOCUMENTS

JP 2005214799 A 8/2005
JP 2005257483 A 9/2005

OTHER PUBLICATIONS

Lange, Analysis of mass spectrometeric data: peak picking and map allignment, 2008, Berlin, pp. 1-212.*
Du, Pan, et al.; Improved Peak Detection in Mass Spectrum by Incorporating Continuous Wavelet Transfor-based Pattern Matching; Bioinformatics Advance Access; Jul. 4, 2006.
(Continued)

Primary Examiner — Elias Desta
(74) Attorney, Agent, or Firm — Sughrue Mion, PLLC (57) ABSTRACT To enable more reliable detection of ion peaks from mass spectral data. Ion peaks are detected from mass spectrum by the following steps. A step of acquiring mass spectral data made up of peaks which is acquired using a mass spectrometer, the peaks having mass-to-charge ratio and intensity information, a step of classifying the peaks in the acquired mass spectral data into a plurality of classes according to the intensity of the peaks, and a step of identifying the peaks as ion peaks or noise peaks based on the intensity information of the peaks which have been classified into the plurality of classes.

9 Claims, 6 Drawing Sheets (56) References Cited

OTHER PUBLICATIONS

Gras, Robin, et al.; Improving Protein Identification From Peptide Mass Fingerprinting Through a Parameterized Multi-Level Scoring Algorithm and an Optimized Peak Detection; Electrophoresis 1999, No. 20, pp. 3535-3550.

Yang, Chao, et al.; Comparison of Public Peak Detection Algorithms for Maldi Mass Spectrometry Data Analysis; BMC Bioinformatics, 10:4, Jan. 2009.

Communication dated Jul. 26, 2016, from the Japanese Patent Office in counterpart application No. 2013-092951.

* cited by examiner

PEAK DETECTION METHOD FOR MASS SPECTROMETRY AND SYSTEM THEREFOR

BACKGROUND OF THE INVENTION

Field of the Invention

The invention relates to a computer program algorithm for identifying and selecting ion peaks from mass spectral raw data and generating a peak list. The invention is directed to an apparatus or a system suitable for performing peak detection automatically such that further protein analysis can be pursued in mass spectrometry.

Description of the Related Art

Generally, a peak detection method has played an important role in protein identification using mass spectrometry. A peak list provides information of precursor ions selected for fragmentation to generate tandem mass spectra by a mass spectrometer. The list also provides information on fragment ions that are dissociated from the selected precursor ions. The information is entered into a protein analysis program, such as database search (DB) or de novo sequencing. The ion peaks in the peak list are used to be matched against amino acid sequences in a database, or to construct an ion series that best represents the peptide provided by a de novo sequencing method, or to thereafter identify the protein from the determined peptide sequences.

In general, the algorithm for picking peaks in peak detection software is to find signal peaks from noise; and ion peaks are usually represented by the mono-isotopic peak if the peak is sufficiently resolved from the other isotopic peaks in the spectra. For the purpose of distinguishingly detecting ion peaks from noise, signal processing techniques are required to reduce noise and resolve ion peaks buried in noise and overlapping peaks. A various computer-based mathematical methods have been applied to improve the resolution of overlapping peaks, to fit models to confirm assumptions from the expected features found in spectra and to recover information not directly observed in the spectra because of the instrumental limitations.

Figure 1:
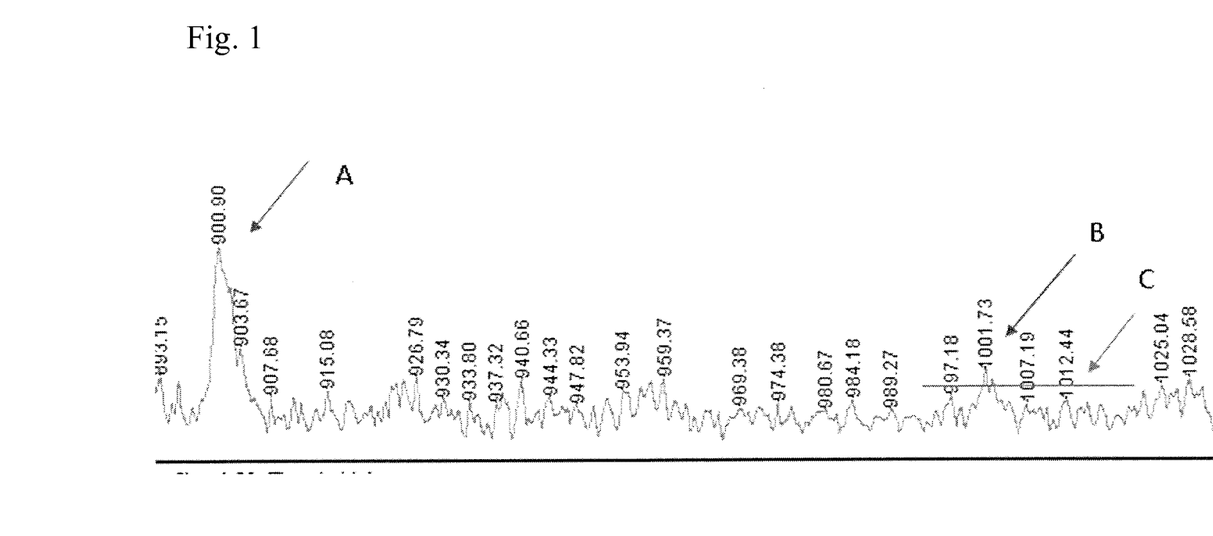
FIG. 1 is an example showing peaks in a mass spectrum.

In using a peak detection computer program in mass spectrometry, all the signal peaks present in a mass spectrum should be found and confirmed through the program, such that a peak list can maximally represent ion information acquired from the experiment. From the existing peak detection software, the derived peak list is often quite short and may contain only a small number of peaks with distinguishing intensity values. It may, on the other hand, be long and contain a large number of peaks including many false positive peaks. For an example, FIG. 1, shows a peak at 900 Da (peak A) of a significantly high intensity. Most peak detection software can easily find and select it as an ion peak. There is another ion peak at 1001 Da (peak B) of a low intensity. This may not be as easy to determine as the previous peak because the intensity for this peak is close to noise peaks in the spectrum. One of the two pieces of existing peak detection software may detect only peak A, but not peak B. The other can detect peak B, but also includes noise peaks, like peak C.

There are also peak detection methods of using an idealized model to fit a spectral profile, and there is certainly a case where the peak shapes may be a key point in finding signal peaks. In these methods, a set of criteria is used to analyse the correlation between the model and spectral data. This works well when peak shapes, such as isotopic peaks in a cluster, are well resolved in the spectra. But when the peaks in a spectrum are of a poor resolution; unreliable correlation from the analysis may be consequently obtained. It becomes difficult to pick correct ion mass peaks or results in real ion peaks being undetected, particularly for those peaks with low intensity. In addition, using this type of method often requires longer computing time to process the whole spectra.

The above peak detection processes and programs are described in Du, P.; Kibbe, W. A. and Lin, S. M.; (2006) Bioinfomratics, 22, 2059-2065, Gras, R.; Muller, M.; Gasteiger, E.; Gay, S.; Binz, P-A.; Bienvenut, W.; Hoogland, C.; Sanchez, J-C.; Bairoch, A.; Hochstrasser, D. F. and Appel, R. D.; (1999) Electrophoresis; 20, 3535-3550, and Yang, C.; He, Z Y. and Yu, W C., BMC Bioinformatics, (2009) 10:4

(1) All the Signal Peaks are Contained in the Peak List While Noise Peaks are Eliminated.

With influences of various factors of instrumentation on the results of experiments, peaks recorded in a spectrum become difficult to identify if the peak shape is distorted from its ideal shape or buried within noise peaks. From a computer program standpoint, it is really a challenge to build an accurate model to reflect these variations. Because of the limitation of method used for identifying ion peaks from spectra, if a peak list contains only peaks with significant intensity from the resolved shapes, some ion information may be lost. In contrast, more noise peaks would be included in order to detect ion peaks with low intensity. The peak lists in both cases do not reflect the best analysis result which would normally be expected from the spectra of a mass spectrometry experiment.

A good database search engine selects expected ions from a peak list to match the proposed ions provided in the sequence database. The problems may be raised in using those peak lists as stated in "Background of the Invention". For a short list where some ion information is lost, the number of ions given in the list is not enough to matching a correct sequence or easy to lead to false hits whereas for a long list including more noise peaks, a wrong ion may be matched by the noise peaks. It also requires a longer time to handle all the peaks in the list. The ambiguity in determining peptide sequence may be even increased when those peak lists are used in de novo sequencing software because the de novo sequencing method usually applies a high quality requirement to the peak list.

(2) Signal Peaks of Low Intensity are Also Detected.

A peak list of sufficient quality contains not only peaks of high intensity but also low intensity and keeps the number of false peaks to a minimum. This requires a peak detection method to determine an accurate noise level present in the spectrum. But this has never been a trivial job in peak detection methods because there are several uncertain factors in finding the distribution of noise. Noise varies depending on what instruments are used, or what mass, or intensity ranges are selected. Inappropriate identification of noise level will generate misleading signals in the peak list. In the existing software, to optimize the selection of ion peaks, various parameters and tolerance values are applied. Thus, more parameters are usually required for the methods. The parameters commonly used include: signal-to-noise ratio, intensity threshold, local maximum and peak width, and so on. If peak shape and distribution are also considered in peak detection, extra criteria are used to judge if a proposed model is fitted to the selected peak. Those parameters are set in the program or determined by the experienced user and entered through an interface. An optimized combination of the parameters may give reasonable results to certain spectra but may not be suitable for applying to other spectra. A test report (Yang et al, 2009) has shown that the effect to increase sensitivity by using those peak detection programs is to bring high false discovery rates. That means more noise peaks represent in the peak list.

With spectral quality varying from experiments and parameters set for different conditions, it is even more difficult to select suitable parameters for all the spectra involved in an analysis, particularly for generating a combination of peak lists in a robust way for high-throughput mass spectrometry data.

SUMMARY OF THE INVENTION

The present invention includes the following aspects.

(1)
An ion peak detection method of detecting ion peaks from peaks present in mass spectral data, including:
acquiring mass spectral data made up of peaks having mass-to-charge ratio and intensity information;
classifying the peaks in the acquired mass spectral data into a plurality of classes according to peak intensity; and
detecting ion peaks from peaks present in mass spectral data based on the intensity information of the peaks which have been classified into the plurality of classes.

(2)
An ion peak detection method according to (1), wherein the plurality of classes according to the peak intensity include a high intensity class, a medium intensity class, and a low intensity class.

(3)
An ion peak detection method according to (2), wherein a noise level is determined from peaks which have been classified into the low intensity class, and the ion peaks are detected from peaks present in mass spectral data based on the noise level.

(4)
An ion peak detection method according to (3), wherein the noise level is determined from peaks which have been classified into the low intensity class as well as from the peaks which have been classified into the medium intensity class.

(5)
An ion peak detection method according to (2), wherein a peak which is an outlier from the low intensity class is classified into the high intensity class.

(6)
An ion peak detection method according to (5), wherein the outlier is obtained by using a Z-score method.

(7)
An ion peak detection method according to (3),
wherein determination of the noise level from the peaks which have been classified into the low intensity class includes
modifying intensity classification of the peaks which have been classified into the low intensity class by comparing a median position of the peaks which have been classified into the low intensity class and a mean signal-to-noise ratio of the peaks which have been classified into the low intensity class, and
determining the noise level from the peaks which have been classified into the low intensity class after the modification.

(8)
An ion peak detection method of detecting ion peaks from peaks present in mass spectral data, including:
acquiring mass spectral data made up of peaks having mass-to-charge ratio and intensity information;
dividing the acquired mass spectral data into given mass ranges;
classifying peaks in a mass range obtained by the dividing into a plurality of classes according to peak intensity; and
detecting ion peaks from peaks present in mass spectral data based on the intensity information of the peaks which have been classified into the plurality of classes.

(9)
An ion peak detection method according to (8), wherein the arbitrary mass range is set to a range chosen from 100 Da to 300 Da.

(10)
An ion peak detection system for detecting ion peaks from peaks present in mass spectral data, including:
peak intensity classification means for acquiring mass spectral data made up of peaks having mass-to-charge ratio and intensity information, and classifying the peaks in the mass spectral data into a plurality of classes according to peak intensity;
noise level determination means for determining noise levels based on the intensity information of the peaks which have been classified into the plurality of classes; and
ion peak detection means for detecting ion peaks from peaks present in the mass spectral data based on the determined noise levels.

(11)
An ion peak detection system according to (10), wherein the plurality of classes according to the peak intensity by the peak intensity classification means include a high intensity class, a medium intensity class, and a low intensity class.

(12)
An ion peak detection system according to (11), wherein a noise level is determined, by the noise level determination means, from peaks which have been classified into the low intensity class, and the ion peaks are detected from peaks present in the mass spectral data based on the noise level.

(13)
An ion peak detection system according to (12), wherein the noise level is determined, by the noise level determination means, from peaks which have been classified into the low intensity class as well as from the peaks which have been classified into the medium intensity class.

(14)
An ion peak detection system according to (11), wherein a peak which is an outlier from the low intensity class is classified into the high intensity class by the peak intensity classification means.

(15)
An ion peak detection system according to (14), wherein the outlier is obtained, by the peak intensity classification means, by using a Z-score method.

(16)
An ion peak detection system according to (10), further including mass range dividing means for dividing the mass spectral data into given mass ranges.

(17)
An ion peak detection system according to (16), wherein the mass range dividing means divides a mass spectrum into ranges chosen from 100 Da to 300 Da.

(18)
An ion peak detection program for causing a computer to perform a process of detecting ion peaks from peaks present in mass spectral data, including:
acquiring mass spectral data made up of peaks having mass-to-charge ratio and intensity information;
classifying the peaks in the acquired mass spectral data into a plurality of classes according to peak intensity; and detecting ion peaks from peaks present in the mass spectral data based on the intensity information of the peaks which have been classified into the plurality of classes.

(19)

An ion peak detection program according to (18), wherein the plurality of classes according to the peak intensity include a high intensity class, a medium intensity class, and a low intensity class.

(20)

An ion peak detection program according to (19), wherein a noise level is determined from peaks which have been classified into the low intensity class, and the ion peaks are detected from peaks present in the mass spectral data based on the noise level.

(21)

An ion peak detection program according to (20), wherein the noise level is determined from peaks which have been classified into the low intensity class as well as from the peaks which have been classified into the medium intensity class.

(22)

An ion peak detection program according to (19), wherein a peak which is an outlier from the low intensity class is classified into the high intensity class.

(23)

An ion peak detection program according to (22), wherein the outlier is obtained by using a Z-score method.

(24)

An ion peak detection program according to (20), wherein determination of the noise level from the peaks which have been classified into the low intensity class includes modifying intensity classification of the peaks which have been classified into the low intensity class by comparing a median position of the peaks which have been classified into the low intensity class and a mean signal-to-noise ratio of the peaks which have been classified into the low intensity class, and determining the noise level from the peaks which have been classified into the low intensity class after the modification.

(25)

An ion peak detection program for causing a computer to perform a process of detecting ion peaks from peaks present in mass spectral data, including:

acquiring mass spectral data made up of peaks having mass-to-charge ratio and intensity information;

dividing the acquired mass spectral data into given mass ranges;

classifying peaks in a mass range obtained by the dividing into a plurality of classes according to peak intensity; and detecting ion peaks from peaks present in the mass spectral data based on the intensity information of the peaks which have been classified into the plurality of classes.

(26)

An ion peak detection program according to (22), wherein the arbitrary mass range is set to a range chosen from 100 Da to 300 Da.

The ion peak detection method of the present invention, the system therefor and the program enable, with respect to a mass spectrum, recognition, and detection, of not only an ion peak of a high intensity, but also an ion peak of a low intensity from noise peaks. A peak list obtained based on ion peaks detected from a mass spectrum by the ion peak detection method of the present invention, the system therefor and the program is useful in database search for protein/peptide or amino acid sequence analysis by the de novo sequencing.

DETAILED DESCRIPTION OF THE PREFERRED EMBODIMENT

Hereinafter, an example of an ion peak detection system according to the present invention for detecting ion peaks in spectral data will be described with reference to FIGS. 2 and 3.

Figure 2:
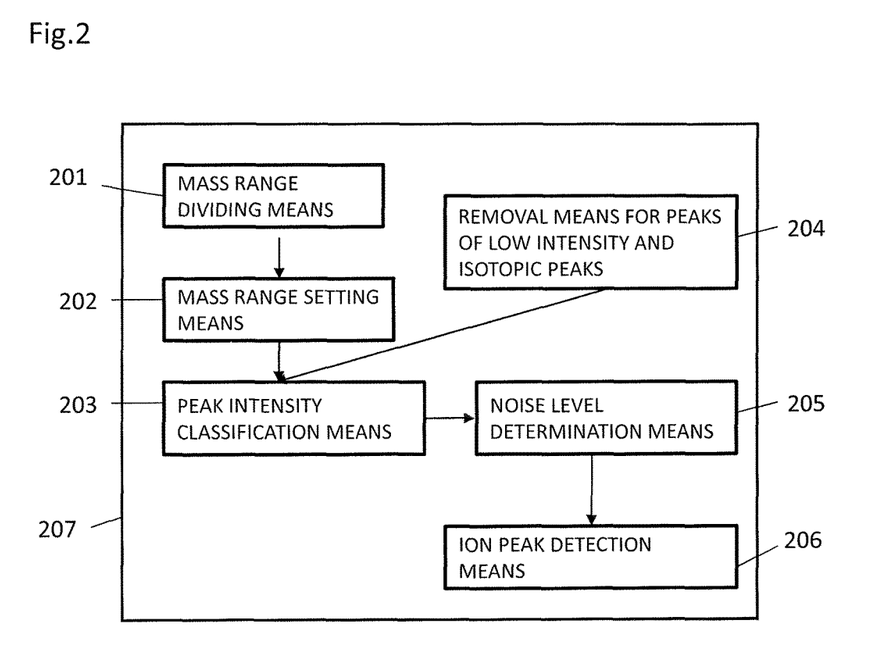
FIG. 2 is a block diagram showing an embodiment of a function of an ion peak detection system of the present invention.

Functions for performing the process of the ion peak detection system of the present example are shown in FIG. 2 as a block diagram. The block diagram includes mass range dividing means 201 for dividing mass spectral data into smaller units according to a given mass range, mass range setting means 202 for setting, as a processing target, a divided mass range or any range in the mass spectrum before dividing, peak intensity classification means 203 for classifying the intensity of peaks present in the set mass range, removal means 204 for peaks of low intensity and isotopic peaks, noise level determination means 205 for determining noise level for the set mass range, and ion peak detection means 206 for generation of a peak list. These means are functions realized by a computer 207. The computer 207 is a dedicated computer provided in a mass spectrometer device or general-purpose computer.

The ion peak detection method and means of the ion peak detection system of the present example will be described according to the flow chart in FIG. 3. First, mass spectral raw data which is acquired by measuring a sample by a mass spectrometer is obtained (step 301). Examples of a sample to be measured may include biological macromolecule such as peptide/protein, nucleic acid and the like. $MS^n$ spectra (n is an integer of one or greater) may be given as the target spectral data. Preferably, $MS^n$ spectra (n is an integer of two or greater) of a peptide/protein sample may be given as the target.

Next, pre-processing (step 302) and removal of isotopic peaks (step 303) are arbitrarily performed on the acquired mass spectral data. These steps are performed by the removal means 204 for peaks of low intensity and isotopic peaks respectively. As the pre-processing of the mass spectral data, there is a process of setting a low noise level (hereinafter, referred to as a first noise level) over the whole mass range in the mass spectral data and removing very low peaks using the first noise level, for example. This first noise level may be set for each of different mass ranges if the noise level varies with mass. For instance, if the mass spectrometer used to acquire the mass spectrum uses Matrix-Assisted Laser Desorption/Ionization tandem Time-of-Flight MS, a so-called MALDI-TOF-TOF, the baseline tends to rise in the high mass range. In such a case, the whole mass range of the processing target mass spectrum is divided into two to five, preferably two, small units to set the first noise level, and the first noise level is set to each unit. This will ensure not too many "low" peaks are removed from a certain mass range.

Very low peaks are filtered using this first noise level.

In the isotopic peak removal (step 303), a process of leaving only the mono-isotopic peaks in a peak group forming an isotopic cluster is performed. A known method can be used as the method of selecting a mono-isotopic peak in an isotopic cluster. For instance, a mono-isotopic peak can be simply selected from the first peak in the peak group forming the isotopic cluster for certain molecule ions, like a peptide and respective fragment ions.

Next, the process proceeds to the step for deciding on an ion peak. The step for deciding on an ion peak includes a mass range setting step (step 304), a noise level determination step of determining a noise level for the set mass range (step 305), and an ion peak detection step (step 306). Each step will be described below.

Figure 3:
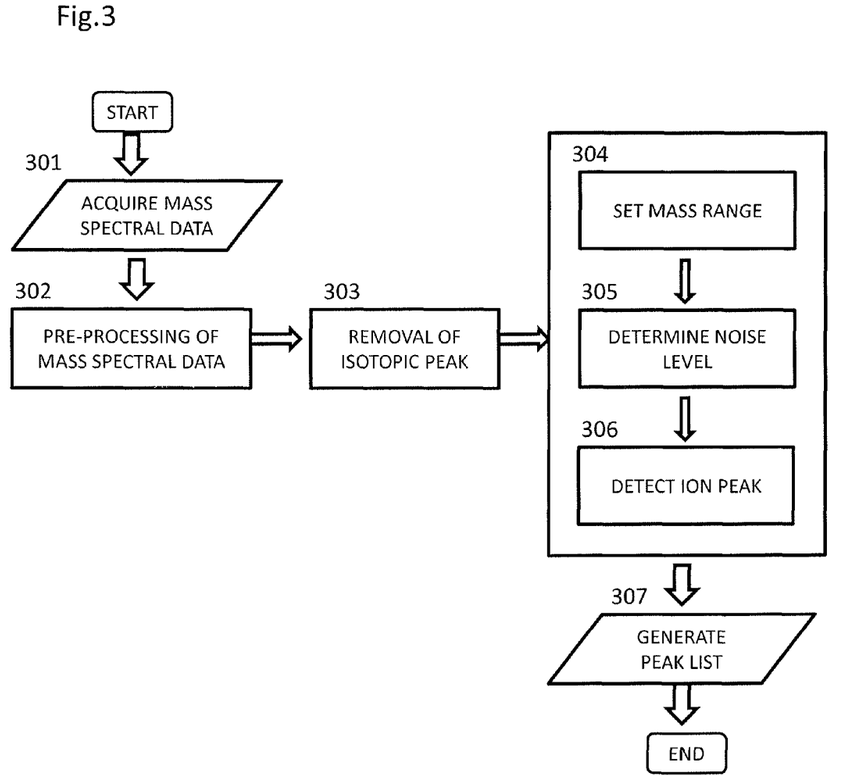
FIG. 3 is a flow chart showing an embodiment of processing steps of ion peak detection performed by the system shown in FIG. 2.

The mass range setting step (step 304) is performed by the mass range dividing means 201 and the mass range setting means 202 in FIG. 3. In this step, a range, in mass spectral data, including at least a mass range which is the target of peak detection processing, is divided into a number of smaller units according to a given mass range, and a mass range for performing the subsequent noise level determination process is set. For example, the MS$^n$ spectral data where n is two or greater is divided into a number of small units from the starting mass to the precursor mass. The range of divided unit, that is, the divided interval, may be chosen from 100 Da to 300 Da, or more preferably, from 100 Da to 200 Da. Or it may be a range chosen from any other smaller values so long as enough peak points are involved in the range. The following example takes a peptide MS$^2$ spectrum as the processing target, and an interval of 120 Da is used to divide the mass range from the starting mass to the high mass end (close to the precursor ion mass). The value of 120 Da is chosen because it is a value close to the average mass of all amino acid residues. When the peptide/protein MS$^n$ spectrum is taken as the processing target, division into a range close to the average mass of amino acid residues, such as from 100 Da to 300 Da, is preferable. The selection of such a range ensures that at least one fragment ion peak is possibly involved in the unit.

In the present invention, mass spectral data which is the processing target is divided into smaller units in the above manner, and the noise level in each mass range which has been set is determined based on the noise peaks present in the range, as will be described below. Then, ion peaks and noise peaks are detected based on the determined noise level, thereby enabling recognition, and detection, of not only the ion peaks of high intensity but also ion peaks of low intensity from the noise peaks.

Here, if the mass range of the processing target mass spectrum is relatively narrow, for example, 300 Da or less, or if there is no great variation in the noise level over a wide mass range, division to smaller units is not necessary, and this mass range dividing step is omitted. In this case, any range in the mass range of the acquired mass spectrum is set as the mass range for the following noise level determination.

Next, the process proceeds to determine the noise level for each mass range which has been set (step 305), and to detect ion peaks present in the mass range (step 306). These steps are performed by the noise level determination means 205 and the ion peak detection means 206. Step 305 is further divided into (i) peak intensity classification and (ii) noise level determination. These are disclosed in more details as follows:

(i) Peak Intensity Classification

A raw mass spectral data includes many peaks having mass-to-charge ratio and intensity information. The peaks may contain noise peaks and ion peaks. Here, an ion peak is an ion-derived signal peak, and a noise peak is a noise-derived peak. In the present step, the many peaks present in the mass spectral data are classified according to the intensity. First, all the peaks contained in the set mass range are arrayed in an ascending order of intensity. The order does not have to be an ascending order, and an order such as a descending order may alternatively be used. The peaks are classified into three classes according to their intensity values. Peaks of significant high intensity compared with other classes are classified into class (A), peaks of medium intensity values are classified into class (B), and peaks of low intensity are classified into class (C). The intensity of peaks classified into class (C) is close to that of peaks classified into class (B), but much lower than that of class (A).

If there are strong ion peaks in the set mass range, the ion peaks are mainly classified into class (A). Class (A) is usually made up of a small number of peaks, and class (C) should contain the majority of the peaks in the set mass range and those peaks are ideally from noise alone. The peaks in class (B) may contain some ion peaks with lower intensity and mix with some noise peaks. In other words, ion peaks of high intensity are classified into class (A), ion peaks of medium to low intensity are classified into class (B), and noise peaks are classified into class (C).

Here, an outlier detection method may be used for the peak intensity classification. This is because if class (C) is categorized as the main class for the peaks contained in the set mass range, the peaks classified into class (A) can be statistically considered as "outliers" (data points far away from other data points) from the main class. Therefore, a common outlier detection method, such as a Z-score method, may be used to determine whether any peaks classified into class (A) can be found. The peaks found in class (A) are temporarily removed at the time of calculation of the noise level determination in the later step, and the noise level is determined from the points in class (C) and maybe some from class (B).

Figure 4:
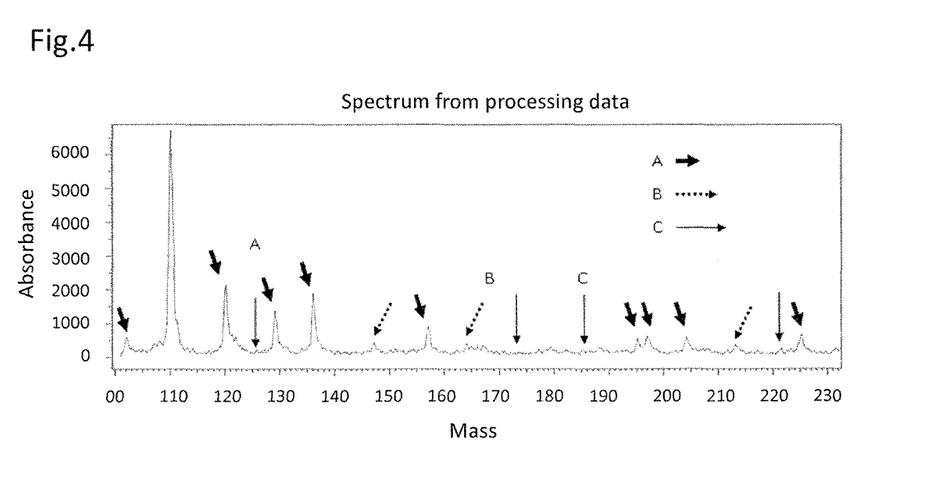
FIG. 4 is an example of a mass spectrum obtained by actual measurement.
Figure 5:
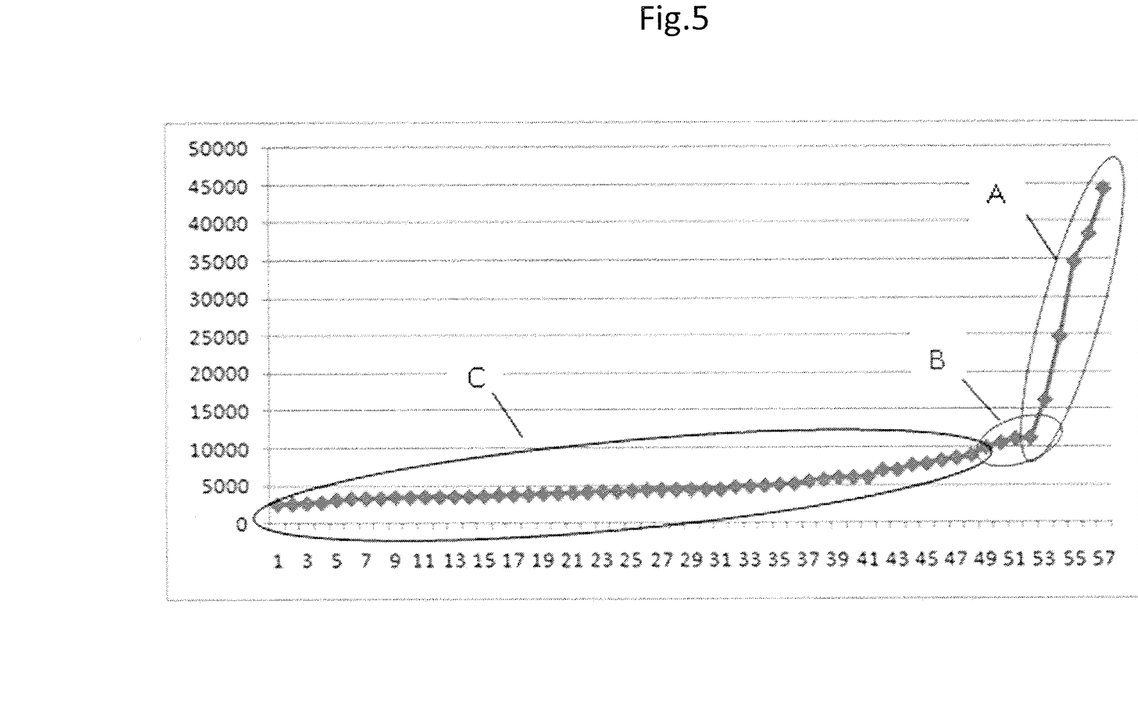
FIG. 5 is a graph where peaks present in the spectral data shown in FIG. 4 are arrayed in the order of intensity.

Here, an explanation will be given with FIG. 4 showing, for an example of intensity classification for peaks in a raw mass spectrum, a mass spectrum obtained by an actual measurement of a given mass range. Peaks present in this range are classified according to these intensity values. FIG. 5 shows a graph where peaks present in the spectral data shown in FIG. 4 are arrayed in the order of intensity. The horizontal axis is the number at the time of arraying the peaks in the order of intensity, and the vertical axis is the intensity of each peak. As shown in FIG. 5, peaks are classified into three classes (A), (B) and (C) in different intensity areas. Here, a case of using the outlier detecting method described above for the peak intensity classification is described. Specifically, here, the Z-score method is used. A Z value obtained for each peak point by calculation may be used as a determination criterion for each point for the classification into class (A) as an outlier.

Now, a $Z_i$ value, which is a Z value of a data point i, is calculated based on the following formula (1) (The calculation of a Z value is shown in Barnett, V.; Lewis, T. Outliers in Statistical Data, 3rd ed.; New York: John Wiley & Sons 1994).

$$Z_i = (|I_i - I_m|)/I_{sd} \quad (1)$$ (Formula 1)

where $I_m$ is the mean value of the intensity values of all the data points, and $I_{sd}$ is standard deviation calculated from the intensity values of all the data points. A data point i in Formula (1) corresponds to a peak i having mass-to-charge ratio and intensity information. Formula modified from Formula (1) using the median absolute deviation $I_{mad}$ defined in Formula (2) may be used instead of $I_{sd}$ (The calculation of modified Z score is shown in Iglewicz, B.; Hoaglin, D.: How to Detect and Handle Outliers, The ASQC Basic References in Quality Control: Statistical Techniques, Volume 16, Edward F. Mykytka, Ph.D., Editor 1993.).

$$I_{mad} = \text{median}(|I_i - I_{median}|) \quad (2)$$ (Formula 2)

wherein $I_{median}$ is the median value of peaks present in the range to which the data point i belongs.

The $Z_i$ value reflects how far a measured value $I_i$ is from the mean/median value. This means the larger the $Z_i$ value, the farther the measured value is from other values. The criterion for deciding an outlier from a Z value is determined by learning from a group of pre-identified data of ion peaks. Through an examination of Z values calculated from the well determined ion peaks, it was found that they were all greater than 3.0. Therefore, the criterion is initialized around this value. The criterion can be adjusted depending on how strong signal peaks are detected in the set mass range. If there is a very strong peak present in the range, the criterion may be increased. After calculating the $Z_i$ value for each peak in the set mass range, the peak points in the set mass range with the Z value exceeding the criterion are classified into class (A). Consequently, the peak points in the set mass range with the Z value below the criterion are classified into class (C). The peak points that should be classified into class (B) are temporarily classified into class (A) and/or (C).

The calculation of Z score also relies on the total number of data in the sample. If the total number in the sample falls below a certain number, this method may not provide a reliable result. Thus, the mass range is set in "SET MASS RANGE" (step 304) to ensure that the number of data is 20 or more, more preferably, 30 or more.

Once the Z value of each peak in the set mass range has been calculated in the above manner, and the peaks in the set mass range have been classified in the above manner, the noise level determination described below is performed.

(ii) Noise Level Determination

The noise level may be found by calculating the mean value of all the noise peaks. Accordingly, the peaks which have been classified into class (A) are removed from the calculation for the noise level determination, and the peaks which have been classified into class (C) in the previous step are used in the calculation for the noise level determination. Here, as noted above, the peak points classified into class (C) in the previous step may include ion peaks of low intensity which should have been classified into class (B) and are not noise peaks. This is because determination of whether a peak of medium intensity should be classified into class (B) or into class (C) is difficult. The present step also allows determination of whether a peak of medium intensity should be classified into class (B) or into class (C). As a consequence, a peak of low intensity can be identified among the noise peaks and can be detected as an ion peak. Ion peak detection (step 306) is carried out depending upon the noise level detected in the set mass range; a parameter, equivalent to a threshold of signal-to-noise (SN) ratio, is used here. A peak having intensity greater than the threshold is considered as a signal peak (an ion peak). In practice, the parameter related to the threshold of signal-to-noise ratio for the ion peak selection is initialized before the step for determining noise level (Step 305). With the determination of noise level, the parameter may be then adjusted according to the results from the detection. The details are disclosed in the following steps.

If all the noise peaks are symmetrically distributed in the set mass range, they can be considered fluctuating around the mean value $I_{mean}$. In an ideal case, if all the peaks involved in the calculation are from noise peaks, the value Formula (3) of the average ratio, $R_{mean}$, for all the data should be a value of 1.0.

(Formula 3)

$$R_{mean} = \sum_{i=1}^{N} R_i / N \quad (3)$$

where $$R_i = I_i / I_{mean} \quad (4)$$ (Formula 4)

Figure 6:
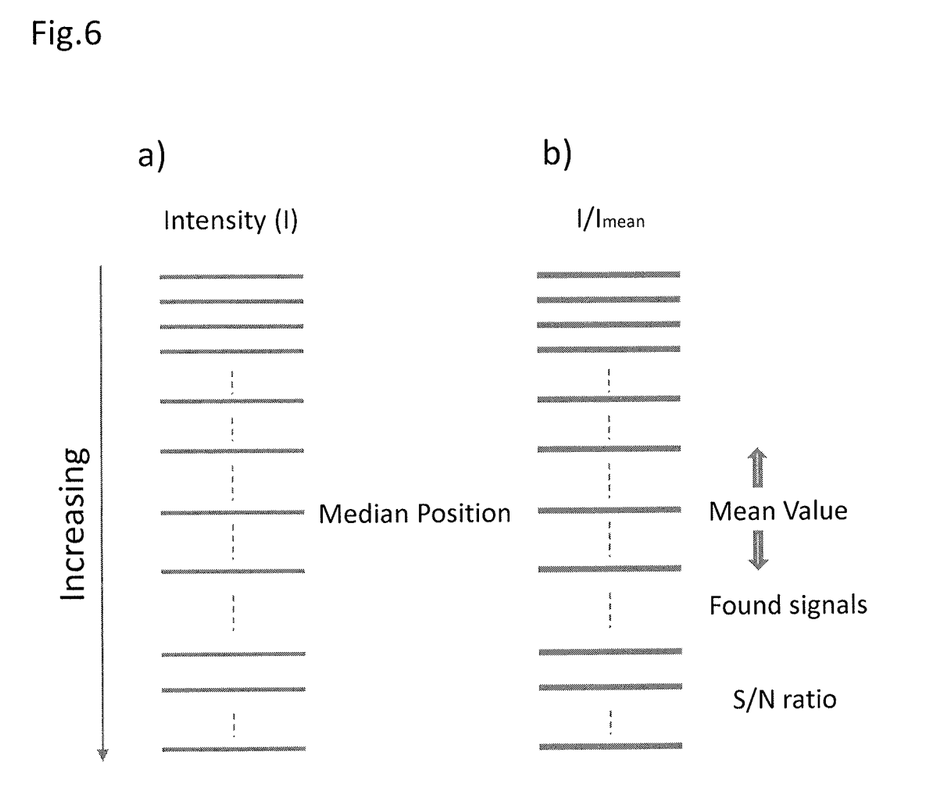
FIG. 6 is a schematic diagram of noise level determination.

In the intensity array where the calculated value $R_i$ for each peak is arrayed in the ascending order of intensity, the position of the ratio $R_i$ closest to the value of 1.0 should be the same as the median position of the intensity array. If the position of the ratio $R_i$ closest to the value of 1.0 is moved down from the median position of the intensity array, it is considered that ion peaks which should be classified into class (B) may be involved in the calculation. This is shown in FIG. 6.

FIG. 6(a) is a diagram obtained by arraying the peaks used in the calculation for noise level determination, that is, the peaks which have been classified into class (C) in the previous step, in the ascending order of intensity and plotting the peaks in the form of bars, and the median position is shown in the drawing. FIG. 6(b) shows a diagram where the $R_i$ of each peak is plotted in the form of a bar at a position corresponding to each peak in FIG. 6(a). $R_{mean}$ is shown in the drawing. As described above, in an ideal case, the median position in FIG. 6(a) and the position of the ratio $R_i$ closest to the value of 1.0 in FIG. 6(b) should be the same. If the noise level found at this condition is said as an idealized position, in most cases, the real noise level will be determined by comparing the positions of two variables, the ratio $R_i$ closest to the value of 1.0 and the median. If the position of the ratio $R_i$ closest to the value of 1.0 is moved down/up from the median position, the noise level is refined from the idealized position accordingly. For example, if the result from the comparison of two variables shows that the ratio $R_i$ closest to the value of 1.0 needs to be moved down a few points, the noise level may be raised from the idealized position. This implies the less number of peaks will be selected as the ion peaks in the range; that is, the peaks that were most likely classified into class (B) are moved to class (C).

On the other hand, the result from the comparison in above step shows that the ratio $R_i$ closest to the value of 1.0 needs to be moved up a few points, the noise level may be lowered from the idealized position. This implies that more number of peaks will be selected in the range; that is, the peaks that were classified into class (C) by Z value are moved to class (B).

Other methods for adjusting the noise level include sequentially eliminating data from the higher intensity, moving the eliminated data to class (A) or (B), and repeating the calculation until the median position and the ratio $R_i$ closest to the value of 1.0 reach to the same point. Thus, class (C) will be made up of only the noise peaks. The peaks classified into class (B) may be detected as the ion peaks, not noise peaks. The mean value in the modified class (C) made up of only noises in the above manner can be further used to determine the noise level.

Other variables/parameters generated in the step of intensity classification are also used to optimize the SN ratio threshold for the selection of ion peaks. This value was initialized. The detected peak features in the set mass range can further adjust it to a more accurate value. These parameters include maximum and minimum Z values, $Z_{max}$ and $Z_{min}$, in the data used for the calculation for noise level determination. Using the modified Z-score formula, $Z_{min}$ is usually a negative value. For a data set symmetrically distributed to their mean value, $Z_{min}$ and $Z_{max}$ should have similar amplitude but in different direction. If the $Z_{min}$ value has large amplitude in the negative direction, this implies that there are more peaks with very low intensities involved in the calculation. In this case, the adjustment is accomplished by lowering the threshold value of SN ratio which was initially set. This is equivalent to move some signal peaks from class (C) to class (B). In contrast, If the $Z_{max}$ value has large amplitude in the positive direction, the peaks which should be classified into class (B) are involved in the calculation, and a noise level higher than the actual value may be derived. In this case, the threshold of SN ratio is raised to eliminate a few peaks that could have been involved in class (A) from the early classification step. Thus, class (C) will be made up of only the noise peaks. This ensures a suitable SN ratio threshold has been correctly assigned.

The noise level determination (step 305) including the peak intensity classification for the set mass range and the noise level determination described above is performed over the mass range of the mass spectral data acquired in step 301.

After the noise level determination, ion peak detection (step 306) is performed. Based on the SN ratio threshold, which may have been further optimized from the results in step 305 of noise level determination, peaks with intensity above the threshold are identified as ion peaks, and peaks with intensity below the threshold are identified as noise peaks. The peaks identified as the ion peaks are recorded in the ion peak list as ion peaks detected in the mass spectrum (step 307).

As described above, the ion peak detection method and the system of the present invention enable, by processing each mass range which has been set, detection of a real noise level that may be present in the mass range from the real data points. In the calculation, several variables are defined, which are related to the signal-to-noise ratio. The parameters used for peak selection are initialized and optimized according to the calculation of those variables. This will allow reflecting real signal and noise distribution in the spectra.

[Another Aspect of the Invention]

In the above described embodiment, for each mass rang which has been set, the ion peak detection (Step 306) is performed after the noise level determination (Step 305), which includes (i) peak intensity classification step and (ii) noise level determination step. However, as described above, classification of the peaks which is performed in (i) peak intensity classification can be modified by the calculation in (ii) noise level determination step so that class (C) will be made up of only the noise peaks, and all the noise peaks will be classified into class (C). In another aspect of the ion peak detection (Step 306), the peaks which are classified into classes (A) and (B) after the modification can be detected as the ion peaks. In this embodiment, the ion peaks can be detected without determining the noise level based on the peaks which are classified into class (C). The modification of the classification which has been performed in (i) peak intensity classification is described in more detail below.

When the result from the comparison of the positions of two variables, the median and the ratio $R_i$ closest to the value of 1.0, which are described above and shown in FIG. 6, shows that the position of the ratio $R_i$ closest to the value of 1.0 is moved up from the median position, at least one peak from the lower intensity among the peaks which have been classified into class (A) by the Z value thereof is moved to class (C). Preferably, sequentially moving the peaks of class (A) from the lower intensity to class (C), the calculation for the comparison is repeated until the median position and the position of the ratio $R_i$ closest to the value of 1.0 reach to the same point. On the other hand, when the result from the comparison of the positions of two variables shows that the position of the ratio $R_i$ closest to the value of 1.0 is moved down from the median position, at least one peak from the higher intensity among the peaks which have been classified to class (C) by the Z value thereof is moved into class (A) or (B). Preferably, sequentially moving the peaks of class (C) from the higher intensity to class (A) or (B), the calculation for the comparison is repeated until the median position and the position of the ratio $R_i$ closest to the value of 1.0 reach to the same point.

The case of using maximum and minimum Z values, $Z_{max}$ and $Z_{min}$, is described next. When the $Z_{max}$ value has large amplitude in the positive direction, at least one peak from the lower intensity among the peaks which have been classified into class (A) by the Z value thereof is moved to class (C). On the other hand, the $Z_{min}$ value has large amplitude in the negative direction, at least one peak from the higher intensity among the peaks which have been classified into class (C) by the Z value thereof is moved into class (A) or (B).

The program of the embodiment of the present invention has been tested on some MS/MS spectral data obtained using MALDI_TOF_TOF. The peak lists generated from the program described in the embodiment of the present invention shown in FIGS. 3 and 4 were input to Mascot database search engine to find MS/MS peptide ion match. These results are compared with the peak lists acquired from existing peak detection software.

Here, three spectra at different degrees of fragmentation are taken as the processing targets. These are sample (I) [YNGVFQECCQAEDK] where sufficient fragmentation is achieved, sample (II) [RPCFSALTPDETYVPK] where medium and sufficient fragmentation is achieved, and sample (III) [DDPHACYSTVFDK] where fragmentation is poor.

The Mascot search results are listed in Tables 1 to 6. (G) shows the results obtained from the peak lists from this program and (F) for the other software. Samples (I), (II) and (III) are taken as the processing targets of I, II and III, respectively. All those peak lists all led to the expected peptides by this search engine. The ions of bolded numbers (underlined) are matched ions. These show ion matches only in the main part (i.e. b, y type ions and the relatives) not including some internal ion fragmentation. It can be seen that for sample (I), both peak lists found more number of main ions (b/y ion). There is a y ion (at 1584 Da) missing from the program (G), but more found for b ions. For sample (II), program F got a peak list by merging two MS/MS spectra fragmented from the same peptide, whereas the result shown in II(G) was derived only from the peak list of better spectrum in two. It is clearly shown from the results that more number of ion peaks can be found from the present program, even from a single spectrum. For sample (III), there are not many ion peaks present in the spectrum. But the result from this program III(G) also show that more matched ions can be found.

TABLE 1

I(G)

| # | Immon. | a | a-17 | a-18 | b | b-17 | b-18 | Seq. | y | y-17 | y-18 | # |
|---|---|---|---|---|---|---|---|---|---|---|---|---|
| 1 | 136.0757 | 136.0757 | | | 164.0706 | | | Y | | | | 14 |
| 2 | 87.0553 | 250.1186 | 233.0921 | | 278.1135 | 261.0870 | | N | 1584.6417 | 1567.6152 | 1566.6312 | 13 |
| 3 | 30.0338 | 307.1401 | 290.1135 | | 335.1350 | 318.1084 | | G | 1470.5988 | 1453.5722 | 1452.5882 | 12 |
| 4 | 72.0808 | 406.2085 | 389.1819 | | 434.2034 | 417.1769 | | V | 1413.5773 | 1396.5508 | 1395.5668 | 11 |
| 5 | 120.0808 | 553.2769 | 536.2504 | | 581.2718 | 564.2453 | | F | 1314.5089 | 1297.4824 | 1296.4984 | 10 |
| 6 | 101.0709 | 681.3355 | 664.3089 | | 709.3304 | 692.3039 | | Q | 1167.4405 | 1150.4140 | 1149.4299 | 9 |
| 7 | 102.0550 | 810.3781 | 793.3515 | 792.3675 | 838.3730 | 821.3464 | 820.3624 | E | 1039.3819 | 1022.3554 | 1021.3714 | 8 |
| 8 | 133.0430 | 970.4087 | 953.3822 | 952.3982 | 998.4036 | 981.3771 | 980.3931 | C | 910.3393 | 893.3128 | 892.3288 | 7 |
| 9 | 133.0430 | 1130.4394 | 1113.4128 | 1112.4288 | 1158.4343 | 1141.4077 | 1140.4237 | C | 750.3087 | 733.2821 | 732.2981 | 6 |
| 10 | 101.0709 | 1258.4980 | 1241.4714 | 1240.4874 | 1286.4929 | 1269.4663 | 1268.4823 | Q | 590.2780 | 573.2515 | 572.2675 | 5 |
| 11 | 44.0495 | 1329.5351 | 1312.5085 | 1311.5245 | 1357.5300 | 1340.5034 | 1339.5194 | A | 462.2195 | 445.1929 | 444.2089 | 4 |
| 12 | 102.0550 | 1458.5777 | 1441.5511 | 1440.5671 | 1486.5726 | 1469.5460 | 1468.5620 | E | 391.1823 | 374.1558 | 373.1718 | 3 |
| 13 | 88.0393 | 1573.6046 | 1556.5781 | 1555.5940 | 1601.5995 | 1584.5730 | 1583.5890 | D | 262.1397 | 245.1132 | 244.1292 | 2 |
| 14 | 101.1073 | | | | | | | K | 147.1128 | 130.0863 | | 1 |

TABLE 2

I(F)

| # | Immon. | a | a-17 | a-18 | b | b-17 | b-18 | Seq. | y | y-17 | y-18 | # |
|---|---|---|---|---|---|---|---|---|---|---|---|---|
| 1 | 136.0757 | 136.0757 | | | 164.0706 | | | Y | | | | 14 |
| 2 | 87.0553 | 250.1186 | 233.0921 | | 278.1135 | 261.0870 | | N | 1584.6417 | 1567.6152 | 1566.6312 | 13 |
| 3 | 30.0338 | 307.1401 | 290.1135 | | 335.1350 | 318.1084 | | G | 1470.5988 | 1453.5722 | 1452.5882 | 12 |
| 4 | 72.0808 | 406.2085 | 389.1819 | | 434.2034 | 417.1769 | | V | 1413.5773 | 1396.5508 | 1395.5668 | 11 |
| 5 | 120.0808 | 553.2769 | 536.2504 | | 581.2718 | 564.2453 | | F | 1314.5089 | 1297.4824 | 1296.4984 | 10 |
| 6 | 101.0709 | 681.3355 | 664.3089 | | 709.3304 | 692.3039 | | Q | 1167.4405 | 1150.4140 | 1149.4299 | 9 |
| 7 | 102.0550 | 810.3781 | 793.3515 | 792.3675 | 838.3730 | 821.3464 | 820.3624 | E | 1039.3819 | 1022.3554 | 1021.3714 | 8 |
| 8 | 133.0430 | 970.4087 | 953.3822 | 952.3982 | 998.4036 | 981.3771 | 980.3931 | C | 910.3393 | 893.3128 | 892.3288 | 7 |
| 9 | 133.0430 | 1130.4394 | 1113.4128 | 1112.4288 | 1158.4343 | 1141.4077 | 1140.4237 | C | 750.3087 | 733.2821 | 732.2981 | 6 |
| 10 | 101.0709 | 1258.4980 | 1241.4714 | 1240.4874 | 1286.4929 | 1269.4663 | 1268.4823 | Q | 590.2780 | 573.2515 | 572.2675 | 5 |
| 11 | 44.0495 | 1329.5351 | 1312.5085 | 1311.5245 | 1357.5300 | 1340.5034 | 1339.5194 | A | 462.2195 | 445.1929 | 444.2089 | 4 |
| 12 | 102.0550 | 1458.5777 | 1441.5511 | 1440.5671 | 1486.5726 | 1469.5460 | 1468.5620 | E | 391.1823 | 374.1558 | 373.1718 | 3 |
| 13 | 88.0393 | 1573.6046 | 1556.5781 | 1555.5940 | 1601.5995 | 1584.5730 | 1583.5890 | D | 262.1397 | 245.1132 | 244.1292 | 2 |
| 14 | 101.1073 | | | | | | | K | 147.1128 | 130.0863 | | 1 |

TABLE 3

II(G)

| # | Immon. | a | a-17 | a-18 | b | b-17 | b-18 |
|---|---|---|---|---|---|---|---|
| 1 | 129.1135 | 129.1135 | 112.0869 | | 157.1084 | 140.0818 | |
| 2 | 70.0651 | 226.1662 | 209.1397 | | 254.1612 | 237.1346 | |
| 3 | 133.0430 | 386.1969 | 369.1703 | | 414.1918 | 397.1653 | |
| 4 | 120.0808 | 533.2653 | 516.2387 | | 561.2602 | 544.2337 | |
| 5 | 60.0444 | 620.2973 | 603.2708 | 602.2868 | 648.2922 | 631.2657 | 630.2817 |
| 6 | 44.0495 | 691.3344 | 674.3079 | 673.3239 | 719.3294 | 702.3028 | 701.3188 |
| 7 | 86.0964 | 804.4185 | 787.3920 | 786.4079 | 832.4134 | 815.3869 | 814.4029 |
| 8 | 74.0600 | 905.4662 | 888.4396 | 887.4556 | 933.4611 | 916.4345 | 915.4505 |

TABLE 3-continued

| II(G) | | | | | | | |
|---|---|---|---|---|---|---|---|
| 9 | 70.0651 | 1002.5189 | 985.4924 | 984.5084 | 1030.5139 | 1013.4873 | 1012.5033 |
| 10 | 88.0393 | 1117.5459 | 1100.5193 | 1099.5353 | 1145.5408 | 1128.5143 | 1127.5302 |
| 11 | 102.0550 | 1246.5885 | 1229.5619 | 1228.5779 | 1274.5834 | 1257.5568 | 1256.5728 |
| 12 | 74.0600 | 1347.6362 | 1330.6096 | 1329.6256 | 1375.6311 | 1358.6045 | 1357.6205 |
| 13 | 136.0757 | 1510.6995 | 1493.6729 | 1492.6889 | 1538.6944 | 1521.6679 | 1520.6838 |
| 14 | 72.0808 | 1609.7679 | 1592.7414 | 1591.7573 | 1637.7628 | 1620.7363 | 1619.7523 |
| 15 | 70.0651 | 1706.8207 | 1689.7941 | 1688.8101 | 1734.8156 | 1717.7890 | 1716.8050 |
| 16 | 101.1073 | | | | | | |

| # | d | d-18 | Seq. | y | y-17 | y-18 | # |
|---|---|---|---|---|---|---|---|
| 1 | 44.0495 | | R | | | | 16 |
| 2 | 200.1506 | | P | 1724.8200 | 1707.7935 | 1706.8094 | 15 |
| 3 | 297.2034 | | C | 1627.7672 | 1610.7407 | 1609.7567 | 14 |
| 4 | | | F | 1467.7366 | 1450.7100 | 1449.7260 | 13 |
| 5 | 604.3024 | | S | 1320.6682 | 1303.6416 | 1302.6576 | 12 |
| 6 | | | A | 1233.6361 | 1216.6096 | 1215.6256 | 11 |
| 7 | 762.3716 | | L | 1162.5990 | 1145.5725 | 1144.5885 | 10 |
| 8 | 889.4713 | 891.4505 | T | 1049.5150 | 1032.4884 | 1031.5044 | 9 |
| 9 | 976.5033 | | P | 948.4673 | 931.4407 | 930.4567 | 8 |
| 10 | 1073.5561 | | D | 851.4145 | 834.3880 | 833.4040 | 7 |
| 11 | 1188.5830 | | E | 736.3876 | 719.3610 | 718.3770 | 6 |
| 12 | 1331.6412 | 1333.6205 | T | 607.3450 | 590.3184 | 589.3344 | 5 |
| 13 | | | Y | 506.2973 | 489.2708 | | 4 |
| 14 | 1595.7523 | | V | 343.2340 | 326.2074 | | 3 |
| 15 | 1680.8050 | | P | 244.1656 | 227.1390 | | 2 |
| 16 | | | K | 147.1128 | 130.0863 | | 1 |

TABLE 4

| II(F) | | | | | | | |
|---|---|---|---|---|---|---|---|
| # | Immon. | a | a-17 | a-18 | b | b-17 | b-18 |
| 1 | 129.1135 | 129.1135 | 112.0869 | | 157.1084 | 140.0818 | |
| 2 | 70.0651 | 226.1662 | 209.1397 | | 254.1612 | 237.1346 | |
| 3 | 133.0430 | 386.1969 | 369.1703 | | 414.1918 | 397.1653 | |
| 4 | 120.0808 | 533.2653 | 516.2387 | | 561.2602 | 544.2337 | |
| 5 | 60.0444 | 620.2973 | 603.2708 | 602.2868 | 648.2922 | 631.2657 | 630.2817 |
| 6 | 44.0495 | 691.3344 | 674.3079 | 673.3239 | 719.3294 | 702.3028 | 701.3188 |
| 7 | 86.0964 | 804.4185 | 787.3920 | 786.4079 | 832.4134 | 815.3869 | 814.4029 |
| 8 | 74.0600 | 905.4662 | 888.4396 | 887.4556 | 933.4611 | 916.4346 | 915.4505 |
| 9 | 70.0651 | 1002.5189 | 985.4924 | 984.5084 | 1030.5139 | 1013.4873 | 1012.5033 |
| 10 | 88.0393 | 1117.5459 | 1100.5193 | 1099.5353 | 1145.5408 | 1128.5143 | 1127.5302 |
| 11 | 102.0550 | 1246.5885 | 1229.5619 | 1228.5779 | 1274.5834 | 1257.5568 | 1256.5728 |
| 12 | 74.0600 | 1347.6362 | 1330.6096 | 1329.6256 | 1375.6311 | 1358.6045 | 1357.6205 |
| 13 | 136.0757 | 1510.6995 | 1493.6729 | 1492.6889 | 1538.6944 | 1521.6679 | 1520.6838 |
| 14 | 72.0808 | 1609.7679 | 1592.7414 | 1591.7573 | 1637.7628 | 1620.7363 | 1619.7523 |
| 15 | 70.0651 | 1706.8207 | 1689.7941 | 1688.8101 | 1734.8156 | 1717.7890 | 1716.8050 |
| 16 | 101.1073 | | | | | | |

| # | d | d-18 | Seq. | y | y-17 | y-18 | # |
|---|---|---|---|---|---|---|---|
| 1 | 44.0495 | | R | | | | 16 |
| 2 | 200.1506 | | P | 1724.8200 | 1707.7935 | 1706.8094 | 15 |
| 3 | 297.2034 | | C | 1627.7672 | 1610.7407 | 1609.7567 | 14 |
| 4 | | | F | 1467.7366 | 1450.7100 | 1449.7260 | 13 |
| 5 | 604.3024 | | S | 1320.6682 | 1303.6416 | 1302.6576 | 12 |
| 6 | | | A | 1233.6361 | 1216.6096 | 1215.6256 | 11 |
| 7 | 762.3716 | | L | 1162.5990 | 1145.5725 | 1144.5885 | 10 |
| 8 | 889.4713 | 891.4505 | T | 1049.5150 | 1032.4884 | 1031.5044 | 9 |
| 9 | 976.5033 | | P | 948.4673 | 931.4407 | 930.4567 | 8 |
| 10 | 1073.5561 | | D | 851.4145 | 834.3880 | 833.4040 | 7 |
| 11 | 1188.5830 | | E | 736.3876 | 719.3610 | 718.3770 | 6 |
| 12 | 1331.6412 | 1333.6205 | T | 607.3450 | 590.3184 | 589.3344 | 5 |
| 13 | | | Y | 506.2973 | 489.2708 | | 4 |
| 14 | 1595.7523 | | V | 343.2340 | 326.2074 | | 3 |
| 15 | 1680.8050 | | P | 244.1656 | 227.1390 | | 2 |
| 16 | | | K | 147.1128 | 130.0863 | | 1 |

TABLE 5

III(G)

| # | Immon. | a | a-18 | b | b-18 | Seq. | y | y-17 | y-18 | # |
|---|--------|---|------|---|------|------|---|------|------|---|
| 1 | 88.0393 | 88.0393 | 70.0287 | 116.0342 | 98.0237 | D | | | | 13 |
| 2 | 88.0393 | 203.0662 | 185.0557 | 231.0612 | 213.0506 | D | 1439.6260 | 1422.5994 | 1421.6154 | 12 |
| 3 | 70.0651 | 300.1190 | 282.1084 | 328.1139 | 310.1034 | P | 1324.5991 | 1307.5725 | 1306.5885 | 11 |
| 4 | 110.0713 | 437.1779 | 419.1674 | 465.1728 | 447.1623 | H | 1227.5463 | 1210.5197 | 1209.5357 | 10 |
| 5 | 44.0495 | 508.2150 | 490.2045 | 536.2100 | 518.1994 | A | 1090.4874 | 1073.4608 | 1072.4768 | 9 |
| 6 | 133.0430 | 668.2457 | 650.2351 | 696.2406 | 678.2300 | C | 1019.4503 | 1002.4237 | 1001.4397 | 8 |
| 7 | 136.0757 | 831.3090 | 813.2985 | 859.3039 | 841.2934 | Y | 859.4196 | 842.3931 | 841.4090 | 7 |
| 8 | 60.0444 | 918.3410 | 900.3305 | 946.3360 | 928.3254 | S | 696.3563 | 679.3297 | 678.3457 | 6 |
| 9 | 74.0600 | 1019.3887 | 1001.3782 | 1047.3836 | 1029.3731 | T | 609.3243 | 592.2977 | 591.3137 | 5 |
| 10 | 72.0808 | 1118.4571 | 1100.4466 | 1146.4521 | 1128.4415 | V | 508.2766 | 491.2500 | 490.2660 | 4 |
| 11 | 120.0808 | 1265.5256 | 1247.5150 | 1293.5205 | 1275.5099 | F | 409.2082 | 392.1816 | 391.1976 | 3 |
| 12 | 88.0393 | 1380.5525 | 1362.5419 | 1408.5474 | 1390.5368 | D | 262.1397 | 245.1132 | 244.1292 | 2 |
| 13 | 101.1073 | | | | | K | 147.1128 | 130.0863 | | 1 |

TABLE 6

III(F)

| # | Immon. | a | a0 | b | b0 | Seq. | y | y* | y0 | # |
|---|--------|---|-----|---|-----|------|---|----|-----|---|
| 1 | 88.0393 | 88.0393 | 70.0287 | 116.0342 | 98.0237 | D | | | | 13 |
| 2 | 88.0393 | 203.0662 | 185.0557 | 231.0612 | 213.0506 | D | 1439.6260 | 1422.5994 | 1421.6154 | 12 |
| 3 | 70.0651 | 300.1190 | 282.1084 | 328.1139 | 310.1034 | P | 1324.5991 | 1307.5725 | 1306.5885 | 11 |
| 4 | 110.0713 | 437.1779 | 419.1674 | 465.1728 | 447.1623 | H | 1227.5463 | 1210.5197 | 1209.5357 | 10 |
| 5 | 44.0495 | 508.2150 | 490.2045 | 536.2100 | 518.1994 | A | 1090.4874 | 1073.4608 | 1072.4768 | 9 |
| 6 | 133.0430 | 668.2457 | 650.2351 | 696.2406 | 678.2300 | C | 1019.4503 | 1002.4237 | 1001.4397 | 8 |
| 7 | 136.0757 | 831.3090 | 813.2985 | 859.3039 | 841.2934 | Y | 859.4196 | 842.3931 | 841.4090 | 7 |
| 8 | 60.0444 | 918.3410 | 900.3305 | 946.3360 | 928.3254 | S | 696.3563 | 679.3297 | 678.3457 | 6 |
| 9 | 74.0600 | 1019.3887 | 1001.3782 | 1047.3836 | 1029.3731 | T | 609.3243 | 592.2977 | 591.3137 | 5 |
| 10 | 72.0808 | 1118.4571 | 1100.4466 | 1146.4521 | 1128.4415 | V | 508.2766 | 491.2500 | 490.2660 | 4 |
| 11 | 120.0808 | 1265.5256 | 1247.5150 | 1293.5205 | 1275.5099 | F | 409.2082 | 392.1816 | 391.1976 | 3 |
| 12 | 88.0393 | 1380.5525 | 1362.5419 | 1408.5474 | 1390.5368 | D | 262.1397 | 245.1132 | 244.1292 | 2 |
| 13 | 101.1073 | | | | | K | 147.1128 | 130.0863 | | 1 |

Through the comparison of search results from two sets of peak lists obtained by different peak detection software, it can be seen that more ion peaks are involved in the peak lists deduced from the peak detection program described in this invention. The database search results also showed reasonable false discovery rates in peptide/protein match by using the peak lists, although the total number of peaks in the peak lists is usually larger compared with those from the other software F.

The invention detects ion peaks from mass spectra. The general principles used in the algorithm may be extended to other types of instruments. In addition, the inventive concept may be suitable for other signal processing in determining noise level.

The present embodiment shows a work-flow performing ion peak detecting in MS/MS spectra acquired from peptide dissociation ($MS^2$ measurement). It is possible to apply the same process to detect ion peak in $MS^3$ spectra acquired by $MS^3$ measurement and so on. Similarly, the same process is also applicable to detect peptide/protein ion peaks in MS spectra.

What is claimed is:

1. An ion peak detection method of detecting ion peaks from peaks present in mass spectral data, comprising:
   acquiring mass spectral data made up of peaks having mass-to-charge ratio and intensity information from a sample using a mass spectrometer;
   classifying the peaks, by a processor, in the acquired mass spectral data into a plurality of classes according to peak intensity, where the plurality of classes include a low intensity class;
   determining a noise level, by the processor, from peaks which have been classified into the low intensity class; and
   detecting ion peaks from peaks present in mass spectral data based on the noise level and
   identifying ions of the sample by comparing the detected ion peaks with proposed ions in a database, whereby identification of the ions of the sample based on the mass spectral data acquired using the mass spectrometer is improved by detecting ions peaks using the noise level.

2. The ion peak detection method according to claim 1, wherein the plurality of classes according to the peak intensity into a high intensity class, a medium intensity class, and the low intensity class.

3. The ion peak detection method according to claim 1, wherein determines the noise level is determined from peaks which have been classified into the low intensity class as well as from the peaks which have been classified into the medium intensity class.

4. The ion peak detection method according to claim 2, wherein a peak which is an outlier from the low intensity class is classified into the high intensity class.

5. The ion peak detection method according to claim 4, wherein the outlier is obtained by using a Z-score method.

6. The ion peak detection method according to claim 1, wherein
   determination of the noise level from the peaks which have been classified into the low intensity class includes modifying intensity classification of the peaks which have been classified into the low intensity class by comparing a median position of the peaks which have been classified into the low intensity class and a mean signal-to-noise ratio of the peaks which have been classified into the low intensity class, and determining the noise level from the peaks which have been classified into the low intensity class after the modification.

7. An ion peak detection method of detecting ion peaks from peaks present in mass spectral data, comprising:

acquiring mass spectral data made up of peaks having mass-to-charge ratio and intensity information using a mass spectrometer;

dividing the acquired mass spectral data into arbitrary mass ranges;

classifying peaks, by a processor, in a mass range obtained by the dividing into a plurality of classes according to peak intensity, where the plurality of classes include a low intensity class;

determining a noise level, by the processor, from peaks which have been classified into the low intensity class;

detecting ion peaks from peaks present in mass spectral data based on the noise level; and identifying ions of the sample by comparing the detected ion peaks with proposed ions in a database, whereby identification of the ions of the sample based on the mass spectral data acquired using the mass spectrometer is improved by detecting ions peaks using the noise level.

8. The ion peak detection method according to claim 7, wherein the arbitrary mass range is set to a range chosen from 100 Da to 300 Da.

9. An ion peak detection system for detecting ion peaks from peaks present in mass spectral data, comprising:

a mass spectrometer that acquires mass spectral data made up of peaks having mass-to-charge ratio and intensity information, and a processor configured to classify the peaks in the mass spectral data into a plurality of classes according to peak intensity, where the plurality of classes include a low intensity class;

determine noise levels based on the intensity information of the peaks which have been classified into the plurality of classes;

determine a noise level from peaks which have been classified into the low intensity class; and detect ion peaks from peaks present in the mass spectral data based on the determined noise levels.

* * * * *